United States Patent [19]

Chen et al.

[11] Patent Number: 5,653,735
[45] Date of Patent: Aug. 5, 1997

[54] IMPLANTABLE CARDIAC STIMULATION DEVICE HAVING AN IMPROVED BACKUP MODE OF OPERATION AND METHOD THEREOF

[75] Inventors: Paris Chuan Chen, Walnut; Dro Darbidian, Tujunga; Min-Yaug Yang, Monterey Park; Samuel M. Katz, Los Angeles, all of Calif.

[73] Assignee: Pacesetter, Inc., Sylmar, Calif.

[21] Appl. No.: 495,915

[22] Filed: Jun. 28, 1995

[51] Int. Cl.$^6$ .................................................. A61N 1/39
[52] U.S. Cl. .................................................. 607/9
[58] Field of Search .................................................. 607/4, 9

[56] References Cited

U.S. PATENT DOCUMENTS

| | | | |
|---|---|---|---|
| 4,337,777 | 7/1982 | Hartlaub et al. | 128/419 PG |
| 4,390,022 | 6/1983 | Calfee et al. | 128/419 PG |
| 4,527,568 | 7/1985 | Rickards | 128/419 PG |
| 4,550,370 | 10/1985 | Baker | 364/413 |
| 4,561,442 | 12/1985 | Vollmann et al. | 128/419 PG |
| 4,690,145 | 9/1987 | King-Smith et al. | 607/63 |
| 4,693,254 | 9/1987 | Mickiewicz et al. | 607/59 |
| 4,712,179 | 12/1987 | Heimer | 364/417 |
| 5,354,316 | 10/1994 | Keimel | 607/4 |

*Primary Examiner*—William E. Kamm

[57] ABSTRACT

An implantable cardiac stimulation device that has automatic functions in each of two different sets of microprocessor operating code. Following implantation, a first mode of operation executes a first set of operating code, stored primarily in RAM, and performs software error detection. Upon detection of an error, the microprocessor is caused to enter a second (backup) mode of operation, where it executes a second set of operating code, which is retained in read-only memory (ROM). Thus, in the unlikely event of error detection, the implantable device is still fully functional in its second mode to provide automaticity, e.g., to select therapies for different heart condition and provide rate-responsive pacing that tracks physiological requirements. If an error is detected in the second mode, than a third mode of operation (e.g., fixed-rate VVI pacing) is enabled.

32 Claims, 8 Drawing Sheets

IMPLANTABLE CARDIAC STIMULATION DEVICE HAVING AN IMPROVED BACKUP MODE OF OPERATION AND METHOD THEREOF

This invention relates generally to implantable devices such as heart pacemakers and, more particularly, to an implantable device that provides automaticity in at least two operating modes, including at least one software backup mode.

BACKGROUND

1. Implantable Devices

Improper operation of the heart can often be remedied by the use of an implantable device, e.g., a pacemaker. These devices generally provide an electrical pulse to a selected area of the heart that is not (in terms of timing or in terms of strength) properly receiving its natural pulse. Using implantable devices, physicians have been able to provide electronic assistance for many different disorders, including pathological bradycardia (abnormal, slow heartbeat), tachyarrhythmia (abnormal, fast heartbeat), and other conditions that can, over time, pose a threat to a patient's life.

Implantable devices generally include three basic elements, i.e., one or more electrodes, a corresponding number of insulated leads, and a control unit.

The one or more electrodes are used to provide electrical stimuli directly to the heart muscle. These stimuli can be pacing pulses, and sometimes can include relatively larger shocks, such as are used to break up tachyarrhythmias. The electrodes are generally threaded directly into the heart muscle and they also can be used to electrically sense heartbeat. In addition to these electrodes, other electrical sensors may be used by the device to sense blood gases, respiration, cardiovolume, temperature, pressure or other physiological conditions.

The insulated leads are used to connect these electrodes with the control unit. The control unit is a relatively large object, and thus must be placed within the chest cavity but away from the heart. The insulated leads are laid within the chest during surgical implantation, and are also used to connect the control unit to the various other sensors, for example, pulmonary sensors at the lungs.

Finally, the control unit includes electrical circuits that generate the pacing pulses from one or more batteries. Modern day devices are sophisticated and include control logic, timing circuits, and input/output ("I/O") circuitry that interfaces the control logic with the electrodes and/or other sensors. For example, the I/O circuitry provides analog-to-digital and digital-to-analog conversion, and it generates the desired electrical stimuli as pulses of the desired strength, duration and frequency. Modern control units typically include a microprocessor and memory, and also are configured to allow remote programming after implantation in the patient's body.

2. Automaticity

Early pacemakers were fixed-rate devices, which provided electrical stimuli to the heart if it failed to beat within a predetermined time period. However, microprocessor-based technology has enabled implantable devices to make complex logical decisions based on a variety of physiological inputs. As examples, modern day implantable devices have the ability to distinguish different types of tachyarrhythmias and to select appropriate therapy that does not impose unneeded trauma on the heart. For example, for some patients, a heartbeat rate of 160 beats per minute might be considered abnormally fast, but it could be both improper and dangerous to associate that condition with a fibrillation condition, which can be treated by applying defibrillation shocks in excess of 500 volts. Such a heartbeat rate could be properly caused by physiological factors, such as stress or exercise. The present day microprocessor-based devices are capable of distinguishing normal physiological conditions from pathological conditions and also of selecting between alternative therapies for the latter. Logical decisions based on physiological variables, choice of therapies responsive to different heart conditions, and automatic self-configuration are examples of what is referred to as automaticity. For specific examples of automaticity, reference is made to a copending and commonly assigned U.S. Pat. No. 5,476,485, filed in the names of Lisa P. Weinberg and Samuel M. Katz on Sep. 21, 1993, and entitled "Automatic Implantable Pulse Generator." That application is incorporated by reference, as though fully set forth herein.

3. Shortcomings

The microprocessor-based implantable devices have proven to be of great practical utility, because they do not impose unneeded trauma on the heart and provide therapy only as needed. However, these devices do occasionally suffer from malfunction and error, albeit this is infrequent and occurs no more frequently than with other modern electronic or microprocessor-based devices. Unfortunately, however, malfunction or error is of significantly greater concern in an implantable device, because a person's life may depend on the device's proper operation. In these devices, errors could be caused by a malfunction in the hardware (the electronics) or by deterioration in the software, which might occur over time.

To minimize the possibility of these errors, many modern implantable devices are provided with fixed-rate circuits implemented in hardware, for use as a backup circuit instead of the microprocessor.. These fixed-rate circuits are triggered upon detection of parity error, and they disable all of the programmable functions of the device, which simply becomes a fixed-rate pacemaker. In other words, in response to detected error, these implantable devices presume that their decision-making circuits are in error and revert to providing a periodic pulses to the heart, losing any automaticity functions that they might have had. Often, the microprocessor is completely shut-down to conserve power, or its operation is ignored and presumed by the circuit to be faulty. An audible alarm within the pulse generator is sometimes sounded, to indicate that the patient should return to a physician's office.

However, under circumstances of software error, it is considered a waste of resources and dangerous to shut-down all of the device's automaticity functions and instead supply fixed-rate pacing to the heart, particularly because the device might be used for tachyarrhythmia or bradycardia detection and therapy, which cannot always be adequately treated by fixed-rate pacing. Otherwise stated, the very reason that the device was implanted in the patient in the first place might have been to address a condition that absolutely requires automaticity.

A further problem in using fixed-rate backup pacing is that the voltage provided to the heart might be set inappropriately high for the particular patient, and therefore might actually interfere with the heart's normal operation. Unfortunately, in an observance of caution, that is exactly how some of today's programmable pacemakers operate. The fact that a software error has been detected does not necessarily mean that the microprocessor-based system is incapable of monitoring the heart's natural operation, of providing automaticity, or of diagnosing and handling potentially dangerous conditions, such as tachyarrhythmia and bradycardia.

Accordingly, there is a definite need for an implantable device that does not shut-down all control and automaticity functions upon detection of an error in operation. Further, there is a definite need to provide these devices with an alternative backup operation that does not impose unneeded trauma on the heart. Further, such a device should be capable of determining the extent of its detected malfunction and whether or not it can continue to operate, implementing fixed-rate pacing either not at all, or only as a last resort. The present invention, as described below, provides such a device.

SUMMARY OF THE INVENTION

The present invention provides an implantable device that meets the aforementioned needs. More particularly, the present invention provides an implantable device that can continue most of its normal functions and operations, including automaticity, notwithstanding detection of certain types of errors. The present invention provides a safer, more reliable implantable device that does not impose unneeded trauma upon the human heart.

In accordance with one form of the invention, an implantable device includes a controller that determines the proper timing of electrical stimuli that should be provided to the heart, and that further includes two memory locations where it can store two sets of operational instructions and data. A first memory location, which can be a programmable, writable memory, is utilized to receive full-featured operating code that can be loaded at the factory or by telemetry. A second memory, which can be a read only storage, stores a second set of operating instructions, to thereby provide a backup that will be used for heart pacing and arrhythmia termination. This second set of code provides automaticity, and the system can switch to it in the event of a detected error in the first set of code.

In a more particular form of the invention, the device can include two parallel memory address pointers, one pointing to RAM or to a combination of both RAM and ROM, and the other pointing just to ROM. These pointers, which can be two alternative vector tables, are respectively used in the normal and software backup operating modes. Alternatively, the second memory can contain compressed code, stored in ROM, that the microprocessor can decompress and load into RAM if a software error is detected. In a further particular feature of the invention, the microprocessor can presume hardware error in the event of a second error detection and only then fall back to fixed-rate pacing as a third, EVVI mode of operation.

The device includes an error-detecting mechanism that can detect corruption of software used to generate the stimuli sent to the heart. This error-detecting mechanism can be anything that detects error in a microprocessor or computer circuit, for example, a parity error mechanism, a watchdog, a checksum mechanism, error correcting codes, a cyclical redundancy checksum, etc., or any combination of them. When a software error is detected, the controller does not shut down, but instead is directed to switch to pacing based upon the second, backup set of operating instructions. The controller thus still can respond to any desired number of physiological inputs, or can provide differing therapies, as determined by the code. The device continues to provide automaticity in this backup mode.

In another form of the invention, the device includes a digital circuit having a novel control structure. A first level of the control is provided by a telemetry circuit, which has the capability of placing the device in a first mode of operation, wherein the controller relies upon a first set of operating instructions and data. A second level of control is provided by a watchdog circuit, i.e., a circuit that ensures that the controller is operating properly by requiring it to periodically acknowledge its operation to the watchdog circuit. If the controller fails to do so, the watchdog circuit presumes hardware error, freezes the controller, and implements a fixed-rate pacing circuit in a third mode of operation. Finally, the software error detecting mechanism provides a third level of control. It monitors the system's software and data being transferred in and out of the RAM for error. If it detects error, it causes the device to switch from the first mode and the first software set to a second mode of operation, where the controller relies upon second set of software, stored as a backup. If the device is already in the second mode, it can inform the watchdog circuit, which then presumes hardware error and implements the fixed-rate pacing. Again, the device provides automaticity in at least two operating modes.

The invention may be better understood by referring to the following detailed description of a particular preferred embodiment, which should be read in conjunction with the accompanying drawings. The detailed description should enable one skilled to build and use one particular implementation of the invention, and it is not intended to limit the enumerated claims, but to serve as a particular example thereof.

BRIEF DESCRIPTION OF THE DRAWINGS

FIG. 4 also illustrates the interrelation of telemetry, error detection, and a watchdog circuit, and control over the preferred embodiment exercised by each of them.

DETAILED DESCRIPTION

The invention summarized above and defined by the enumerated claims may be better understood by referring to the following detailed description of a particular preferred embodiment, which should be read in conjunction with the accompanying drawings. This detailed description should enable one skilled in the art to build and use one particular implementation of the invention, and it is not intended to limit the enumerated claims, but to serve as a particular example thereof. The particular example set out below is the preferred specific implementation of the invention, namely an implantable device that assists a heart by providing pacing, anti-tachyarrhythmia, anti-bradycardia or other therapy.

1. Introduction to the Principal Parts a. Hardware

Figure 1:
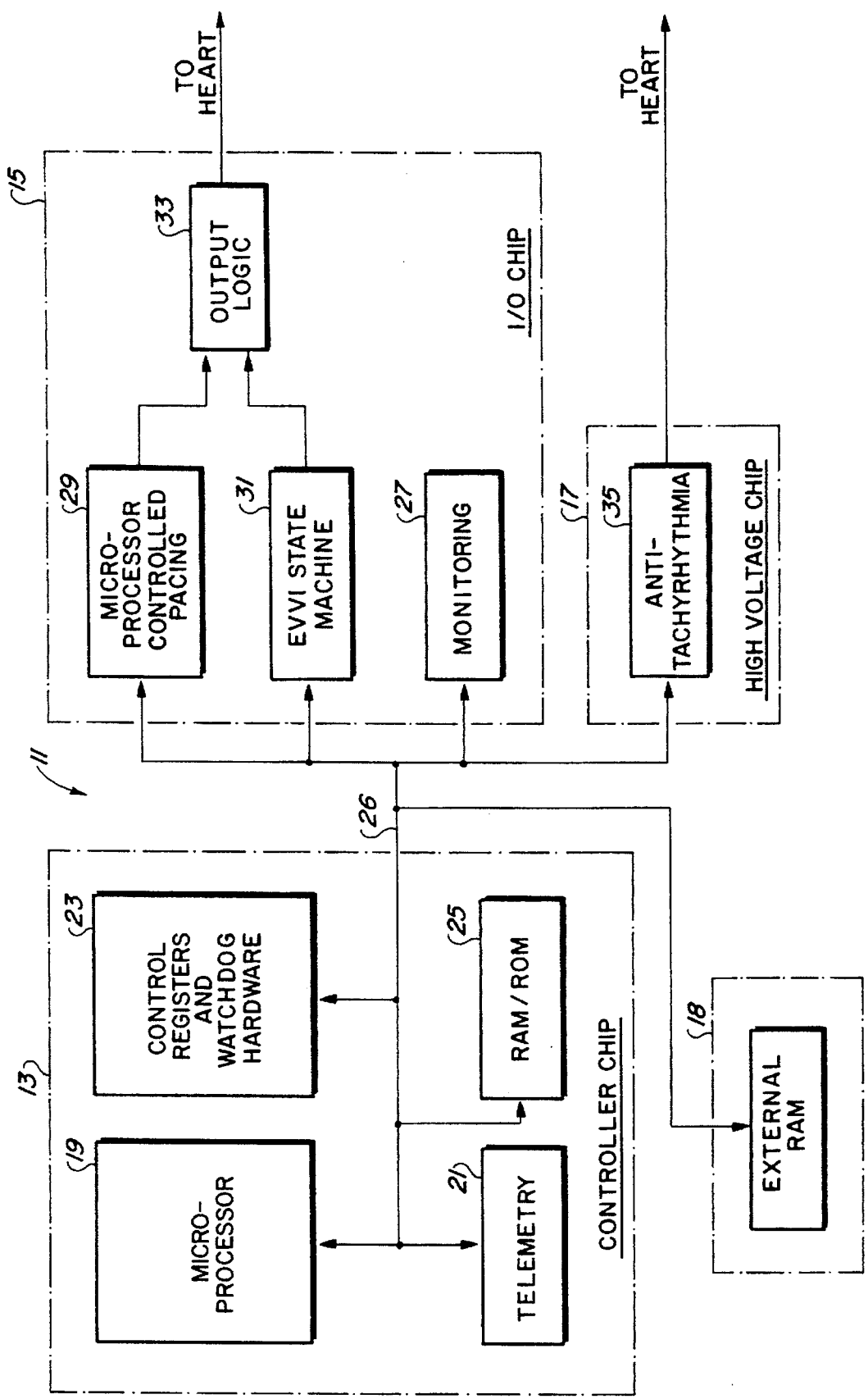
FIG. 1 illustrates the major functional blocks of the preferred implantable device, in terms of chip layout. In particular, four principal chips of the device include a controller chip, an I/O chip, a high voltage chip, and an external RAM chip.

FIG. 1 shows the general layout of a control unit 11 of the preferred implantable device. As shown in FIG. 1, the control unit has four principal chips, including a controller chip 13, an input/output chip 15, a high-voltage chip 17, and an external random-access memory ("RAM") chip 18. The functions and inter-relation of these chips are briefly introduced as follows.

The controller chip 13, shown at the left side of FIG. 1, makes most of the device's logical decisions. To this effect, it includes a microprocessor 19 (e.g., the preferred "controller"), a telemetry circuit 21, other circuit elements including control registers and watchdog hardware 23, and an internal memory element 25 that stores a second set of operating code for the microprocessor, as will be explained below. Communications both between these elements and with the other circuits of the control unit 11 are sent via a system bus 26.

The input/output ("I/O") chip 15 is shown at the upper right of FIG. 1, and it provides input and output functions for the controller chip 13. In addition, the I/O chip also implements EVVI pacing in lieu of microprocessor-controlled pacing, in the unlikely event of a hardware error or a second software error. More particularly, the I/O chip 15 provides three circuit paths to the heart. First, monitoring logic 27 of the I/O chip receives sensory inputs from the heart or from other sensors, e.g., blood gas sensors and respiration sensors. In the preferred control unit 11, input signals coming only from the heart are used, and the microprocessor 19 relies upon heartbeat analysis of these input signals to distinguish physiological tachycardia from pathological tachycardia.

The second and third paths to the heart are outputs from the control unit 11, and they are provided respectively by microprocessor-controlled pacing circuitry 29 and an EVVI state machine 31. These elements directly control output logic 33, which is the hardware that actually generates the electrical stimuli for the heart. The microprocessor-controlled pacing circuitry is used by the microprocessor 19 to directly control the output logic using logic signals supplied by the microprocessor. In the case of microprocessor or hardware failure, the EVVI state machine 31 is conditioned to directly control the output logic, in accordance with hardwired values. The output logic thus always is used, whether it is receiving its instructions from the microprocessor or the EVVI state machine, and it generates pulses in response to one or the other.

The high-voltage chip 17, which is shown at the lower right of FIG. 1, is relied upon principally to provide anti-tachyarrhythmia therapy to the patient's heart. For example, a serious condition such as ventricular fibrillation ("VF") can require large electrical shocks (e.g., several hundred volts) to arrest the VF condition and save the patient's life. The microprocessor 19 detects such a life-threatening condition and to responsively controls anti-tachyarrhythmia circuitry 35 of the high-voltage chip. However, this control is sophisticated, and it can vary substantially depending upon the particular condition detected by the microprocessor. The particular therapy applied is determined by one of two alternative sets of the microprocessor's operating code. The high voltage chip actually includes additional circuitry on the hybrid which is used for generating the high voltages used therapeutically. Whenever used in the specification, high voltage chip includes this additional circuitry.

Less dangerous, but still significant, tachyarrhythmia conditions also can be diagnosed, and differing therapies are provided, depending upon the condition. For example, the microprocessor 19 can be programmed to cause the I/O chip 15 to apply relatively few, small (e.g., 10 volt) shocks to the heart if the heartbeat rate is detected to be above 150 beats-per-minute ("BPM"). Alternatively, a heartbeat rate detected to be above 260 BPM could be indicative of fibrillation and might call for stronger (e.g., 500 volt) and more numerous shocks, provided by the high-voltage chip 17.

By diagnosing different conditions and providing therapy dedicated to different conditions, the preferred implantable device does not impose unneeded trauma to the heart by imposing larger shocks or more traumatic therapy when such is not needed. In addition, since the most significant life-saving function of the preferred device is to provide anti-tachycardia therapy, a second, backup microprocessor mode, discussed below, permits the microprocessor 19 to retain this vital function notwithstanding a detected software error.

b. Modes of Operation

Figure 2:
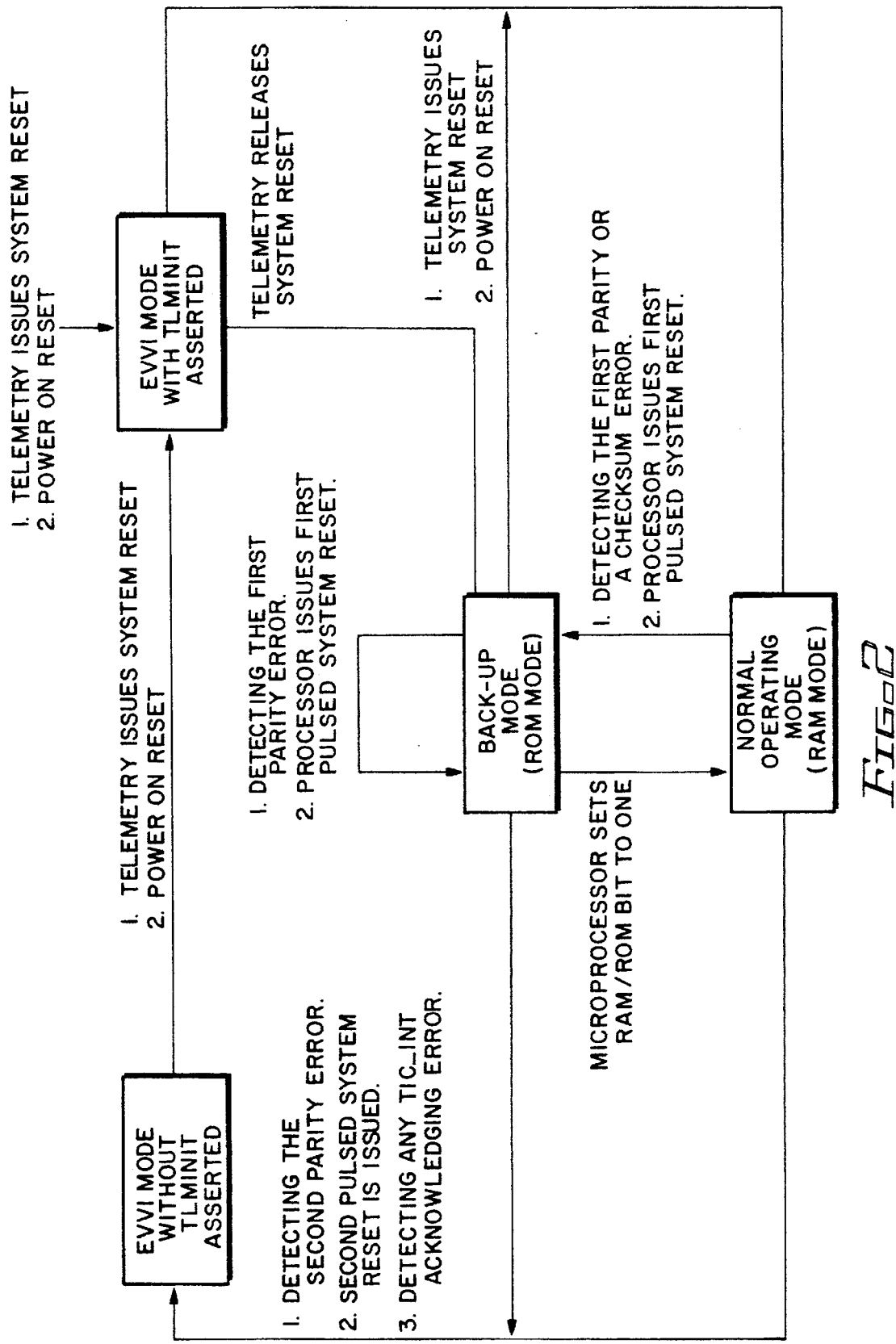
FIG. 2 is a software block diagram illustrating the various modes of the preferred embodiment and switching between these modes, in response to specified factors.

With initial reference to FIG. 2, the operation of the software of the preferred implantable device will be introduced. The microprocessor 19 is provided with two alternative sets of software, each of which provides automaticity. The preferred device, in fact, provides three operating modes, which are diagrammatically indicated in four blocks of FIG. 2, from bottom to top. A first, normal operating mode (the "RAM" mode, indicated in the bottom-most block) uses a first software set, while a second, backup operating mode (the "ROM" mode, shown in the middle of FIG. 2) uses a second, alternative set of software. Finally, a third, fixed-rate ("EVVT") mode also is used. FIG. 2 actually shows this third mode in two blocks at the top of FIG. 2; the third mode can be entered, as shown at the top left side of FIG. 2, in the event of detected hardware error or a second software error. As shown at the top right side of FIG. 2, the third mode also can be entered when telemetry is used to program the system and disable the logic functions, for system diagnosis and re-programming. Automaticity functions, including the diagnosis and treatment of tachyarrhythmia and bradycardia, are provided in each of the first and second modes, whereas in the third mode, automaticity is not provided for, and fixed-rate pacing is provided under hardware control. The microprocessor is not used in the third mode.

In the first mode (represented by the bottom-most block of FIG. 2), the microprocessor 19 operates on the first set of software, which is located primarily in the external RAM chip 18 of FIG. 1. To access this set of software or operating code, the microprocessor is supplied with a first memory address pointer (i.e., a first vector table) that directs the microprocessor to utilize the external RAM chip for most automaticity functions, and the internal memory element 25 of FIG. 1 for certain functions common to both of the first and second modes, e.g., for software that causes the microprocessor to interface with the watchdog and control registers.

In the second, backup mode (the middle block of FIG. 2), which is the default mode for the microprocessor 19 when the implantable device is first implanted in a patient, the microprocessor operates upon the second set of software, which consists of operating instructions and data that are stored in the internal memory element 25 of the controller chip 13 of FIG. 1. As will be explained below with reference to FIG. 3, this memory element includes an instruction set ROM 37, an internal workspace RAM 38, and a 64-byte vector ROM 40. The second set of operations code is stored in the instruction set ROM 37, whereas data and parameters can be loaded into the internal RAM 38, either by the second set of software or by telemetry.

Like the first set of software, the second, alternate set of software also provides for automaticity functions, which can be the same functions provided for by the first set of software, or a subset of them. The second set of software could provide different functions, and preferably is a factory standard set of three anti-tachyarrhythmia therapies and one anti-bradycardia therapy. In any event, the first and second modes both preferably rely upon some common software that is stored in the instruction set ROM 37, such as to interface with the control registers and watchdog hardware 23 of FIG. 1. After the implantable device has been initially implanted, it can be switched by telemetry to operate in the first mode.

During operation of the implantable device in the first mode, an error detecting mechanism is relied upon to cause the device to switch from the first mode to the second mode or the third mode. As indicated in FIG. 2, if the error detecting mechanism detects a software error when the device is operating in the first mode, the microprocessor 19 is reset such that it begins operating in default, i.e., the second, backup mode. In the second mode, the microprocessor looks to a second vector table that points only to the internal memory element 25 of FIG. 1. The microprocessor can still, in this mode, utilize the internal RAM for storing sensed parameters and variables, but its operating instructions are obtained only from the instruction set ROM 37, as commanded by the second vector table.

As indicated at the left-hand side of FIG. 2, if a second software error is thereafter detected, or if a hardware error is detected at any time, the error detecting mechanism causes the device to enter the third, EVVI mode of operation. The device will thereafter supply only fixed-rate pacing until telemetry is used to take the device out of the third mode.

2. The Layout of the Controller Chip 13

Figure 3:
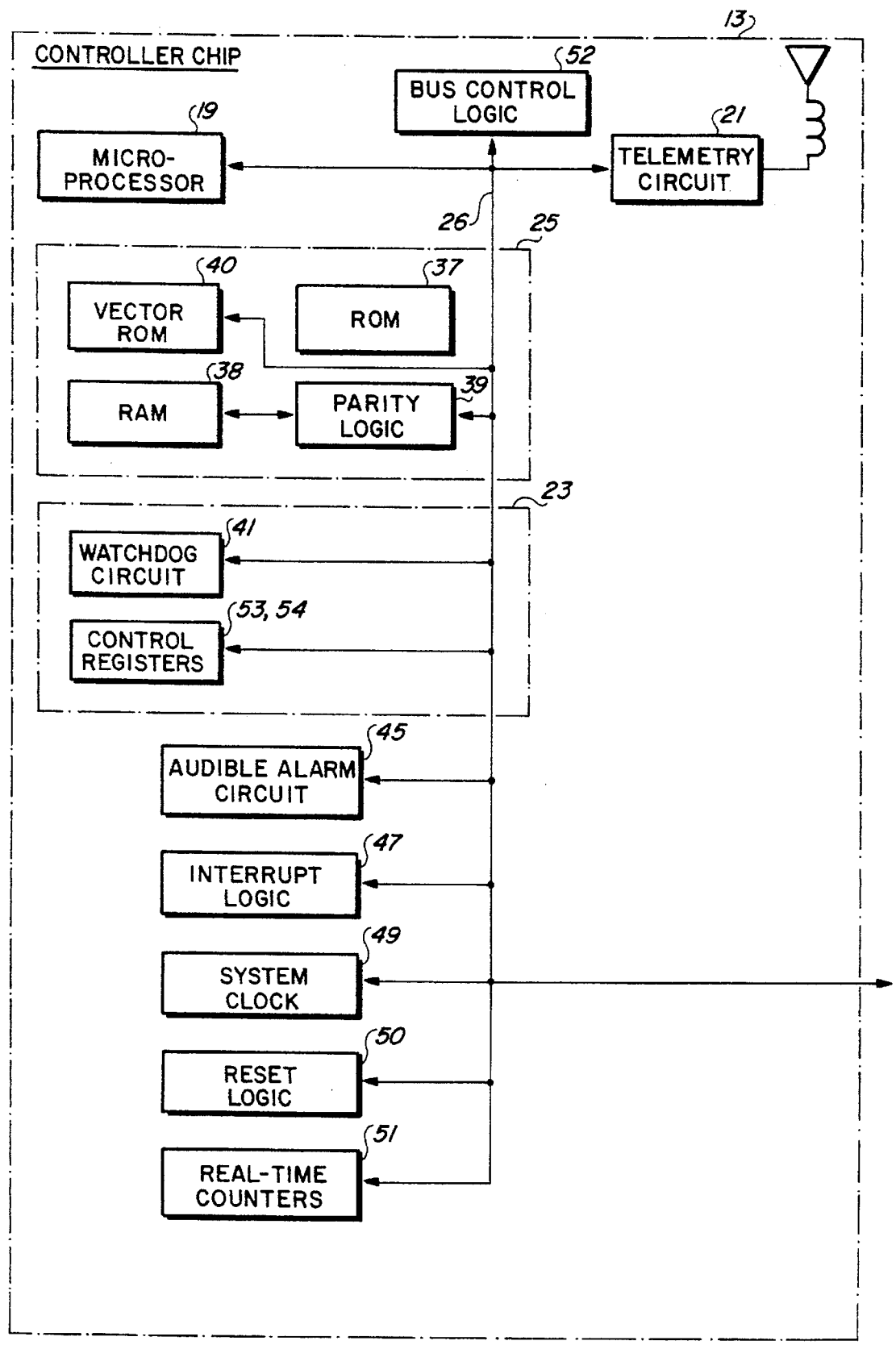
FIG. 3 is a hardware block diagram of the controller chip 13 of FIG. 1.

With reference to FIG. 3, the controller chip 13 is shown to include several important logic elements that have been placed together on a single chip. Principal among these elements is the microprocessor 19, which is an 8-bit microprocessor that runs on a one megahertz clock. It is supported by peripheral logic and several internal memory elements, including the instruction set ROM 37, the internal RAM 38, and the 64-byte vector ROM 40, which all are part of the controller chip's internal memory element 25. In addition to these elements, the controller chip also features parity logic 39, which checks the parity of parameters as they are retrieved from the internal RAM 38. The parity logic is one part of the error detecting mechanism used to switch the modes of the device according to the present invention. If the parity logic detects an error, it notifies a watchdog circuit 41, which in turn causes the implantable device to enter the second mode.

Figure 6:
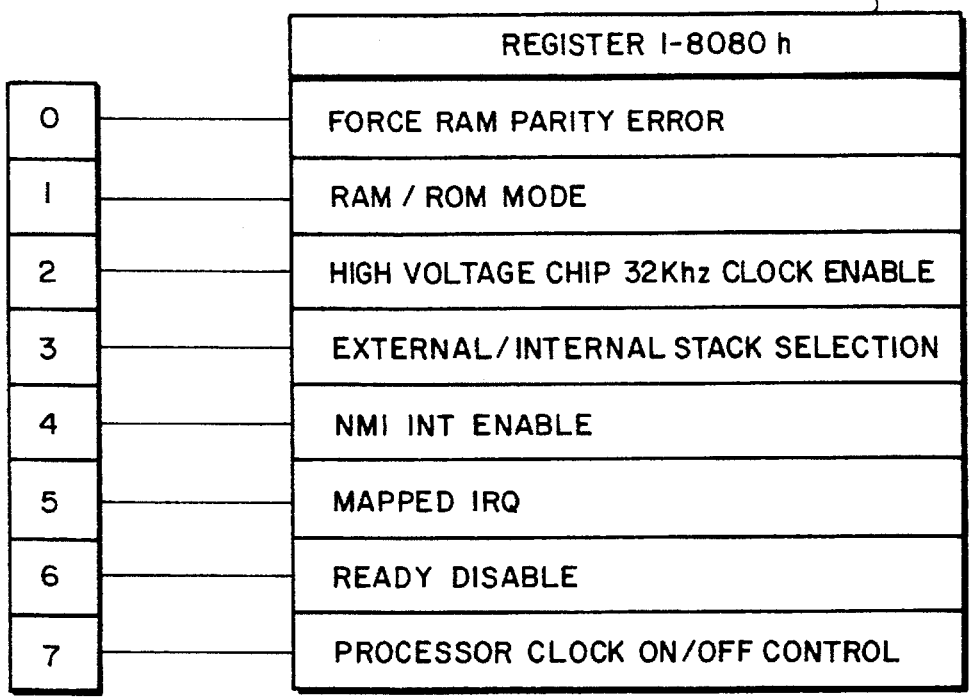
FIG. 6 indicates functions associated with the various bits of a first control register, which is located at memory location 8080 (hex) in the preferred embodiment.
Figure 7:
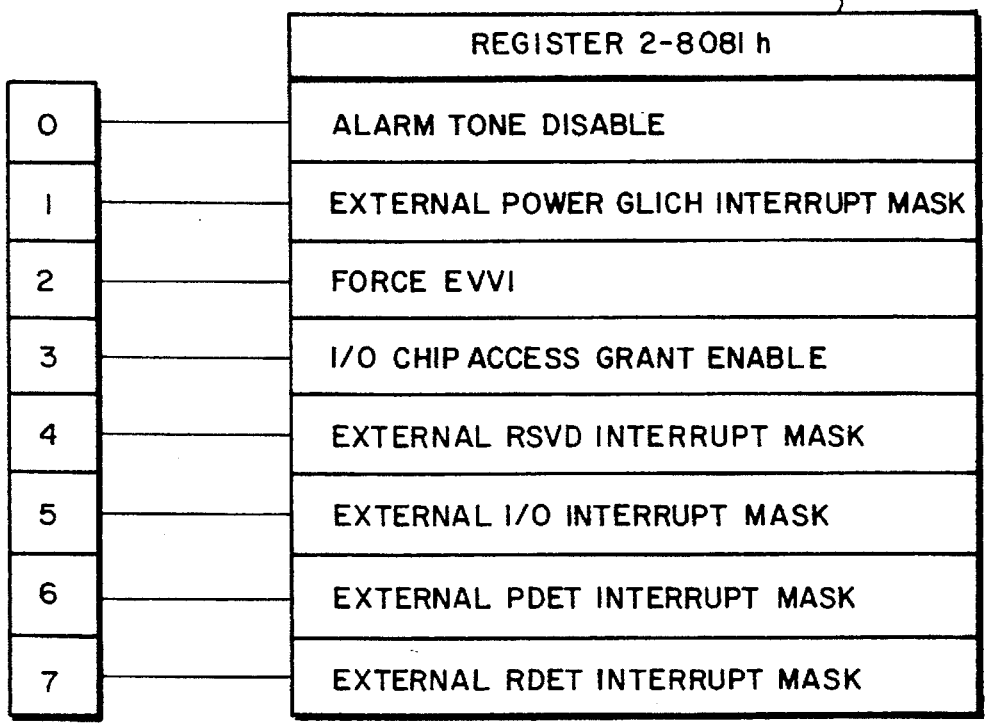
FIG. 7 indicates functions associated with the various bits of a second control register, which is located at memory location 8081 (hex) in the preferred embodiment.

The controller chip 13 also features additional logic elements that assist the operation of the device. For example, an audible alarm circuit 45 alerts the patient that the device requires attention, for example, when battery power is low, or that the high-voltage chip 17 is preparing to deliver a charge. The configuration of the audible alarm circuit will be discussed further below. As with other microprocessor-based systems, the device includes interrupt logic 47, a system clock 49, reset logic 50, and real-time counters 51, the latter being used to measure time periods as directed by software. Finally, the controller chip also includes a set of control registers 53 and 54, which provide various functions as illustrated by FIGS. 6 and 7 and, as will be discussed below.

Read and write control of the various logic elements of the control unit 11 is provided to both the microprocessor 19 and the telemetry circuit 21, and to this effect, bus control logic 52 is employed to grant access to the system to these elements. The microprocessor and the telemetry circuit share the same system bus 26, but they do not share all of the bus control logic. The telemetry circuit has higher priority to use the system bus; hence, when telemetry is being used to access the bus, access by the microprocessor to the system bus is inhibited.

3. Memory Allocation

In accordance with the present invention, the operating code for the first set of software for the microprocessor 19 is stored in the external RAM chip 18, and the operating code for the second set of software is stored as firmware in the instruction set ROM 37 of the controller chip 13. A general memory map for the microprocessor is included as Appendix "A," and it provides information as to the various memory elements used by the microprocessor.

As indicated in Appendix "A," the external RAM chip 18 of FIG. 1 has storage space for approximately 16,000 bytes of software, whereas the instruction set ROM 37 (FIG. 3) is only about half that size. This is because in the preferred embodiment, the external RAM chip is used as a first memory location for full-featured software that can be tailored to the patient's condition and can provide many specialized functions. By contrast, the primary purpose of the preferred backup firmware stored in the instruction set ROM is to provide default, un-tailored, tachyarrhythmia and bradycardia detection and therapy. As mentioned earlier, software error is extremely rare and, thus, the preferred implantable device will almost always operate in its first, RAM mode. However, the backup firmware, firmware being defined as software stored in ROM, provides additional life-security in the event of a software error. If an unlikely error is detected, the control unit 11 will sound an alarm to indicate that the patient should contact his or her physician, so that the error can be properly addressed.

Preferably, both sets of code are programmed into the system during manufacture. As programmed in the factory the device is left in a storage mode, in which it provides null values as a pacing output and returns null values as sensory inputs. Thus, when operating in this manner, the device provides no stimuli and uses little power. While on the shelf and prior to implantation, its battery life is not significantly reduced. At implantation, the device is configured via the telemetry circuit 21 so as to provide actual pacing stimuli. Further, the telemetry circuit is utilized to load, if necessary, new software and parameters into the external RAM chip 18 or the internal RAM 38.

Certain critical basic software functions (not illustrated in the accompanying figures) are required for both the first and second modes of operation, and they are stored in the instruction set ROM 37 regardless of the current mode. Examples of these critical basic functions are:

1. A watchdog acknowledgement routine.
2. A telemetry mailbox service routine (protocol).
3. A routine for the checksum operation.
4. A reset routine, as well as other small functional routines.

Certain features of these routines considered important to an understanding of the preferred embodiment are discussed below, most notably, the features which relate to correct watchdog acknowledgment. Otherwise, it is believed that the precise structure of the four mentioned routines will vary depending upon the particular implementation and can be easily written by one having ordinary skill in logic design.

4. Control Over Modes of Operation

When the telemetry circuit 21 has access to the system, it can be used to change the mode of the implantable device, e.g., place it in any of the first, second or third modes. It does this by causing the microprocessor 19 to configure its control registers, including registers 53 and 54, which are detailed in FIGS. 6 and 7. Importantly, the second least significant bit of the control register 53, labeled in FIG. 6 as "RAM/ROM mode," indicates whether the device is operating in the first, RAM mode or the second, backup ROM mode. When the bit is set to "1," the microprocessor will look to a first vector table using the bit together with pointers located at 80E0-80FF hex (a range of memory locations), and determine that its non-administrative functions are defined in the external RAM chip 18 at address locations 0300-3FFF hex. Alternatively, if this bit is set to "0," as it is upon a power-on reset, the device operates in the second mode, and the microprocessor determines from the bit that it must look to a second vector table, which points only to the ROM 37 (A000-BFFF hex), for all of its functions. Importantly, whichever vector table the microprocessor uses will always direct it to the instruction set ROM 37 for the four routines mentioned above, including the watchdog acknowledgement routine.

Both of the vector tables are stored in the 64-byte vector ROM 40, which also is located on the controller chip 13. The upper 32 bytes of this latter memory are used to store interrupt vectors to be used as part of the first, RAM mode interrupt service routine pointers. By contrast, the lower 32 bytes contain corresponding pointers to be used in the second, ROM mode; these latter pointers instead direct the microprocessor 19 to the second instruction set. The vector ROM can be accessed by the microprocessor 19 using a data fetch and a vector fetch.

Figure 4:
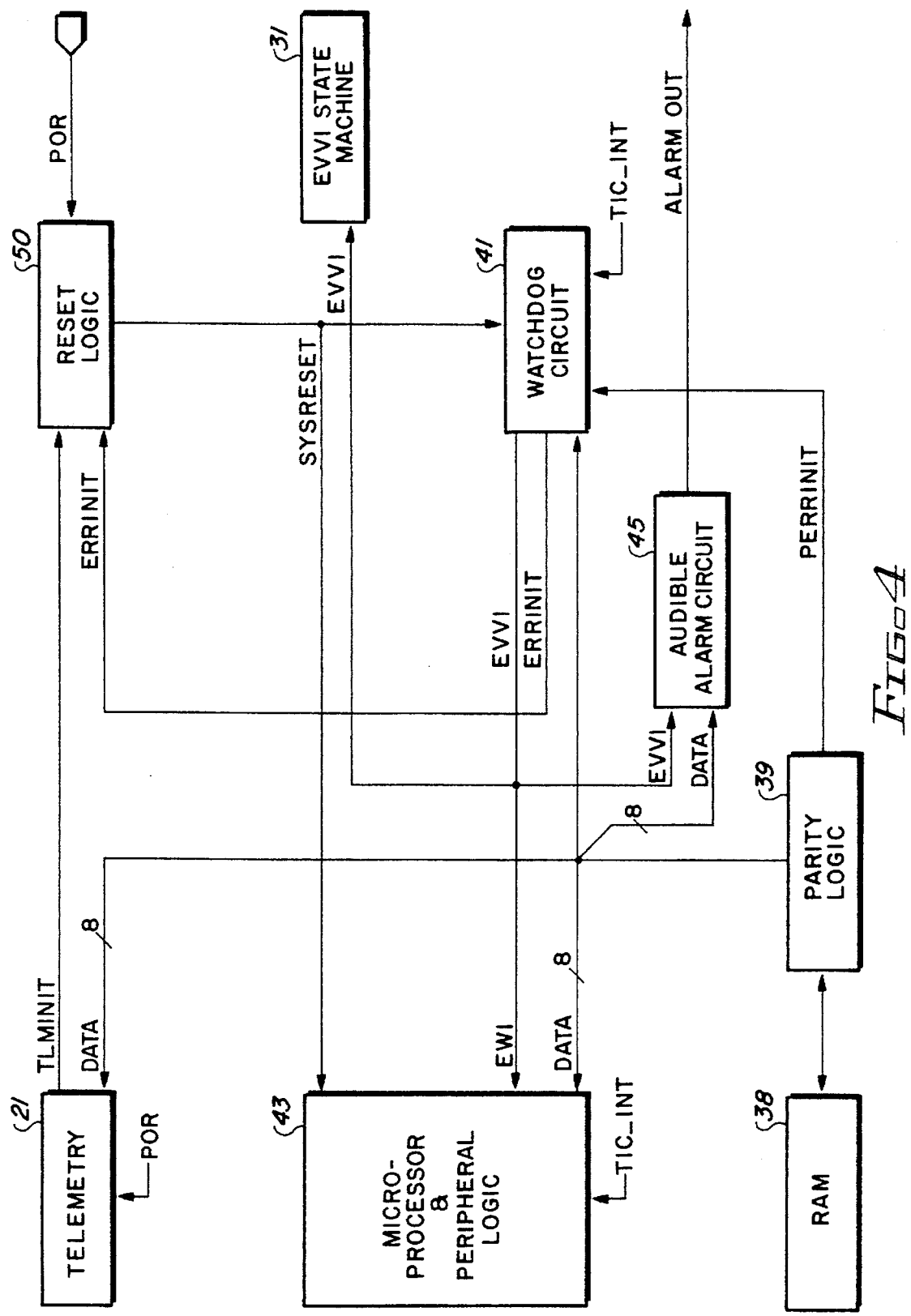
FIG. 4 is a hardware block diagram that illustrates the use of microprocessor-resets and error detection mechanisms of the present invention.

Referring now to FIG. 4, the use of microprocessor resets and error detection mechanisms will be described. Reset logic 50 is employed to interrupt the microprocessor 19 and peripheral logic 43 by providing a system reset signal (labeled "SYSRESET" in FIG. 4) after a first software error has been detected. This causes the microprocessor and peripheral logic to set the "RAM/ROM mode" bit either with a logical "1" if the telemetry circuit 21 has just written a special code to the internal RAM 38, or to leave it at the default value of a logical "0," otherwise. If the RAM/ROM mode bit is set to zero, the microprocessor will thereafter operate only upon the ROM code as directed by the second vector table. If the system reset represents a second error, the system is placed in the third mode of operation (where fixed-rate pacing is applied) when the watchdog circuit 41 freezes the microprocessor clock with its "EVVI" signal. This can also be forced by telemetry, which can cause reset logic to raise the system reset and keep it raised. This freezes the operation of the microprocessor, and the watchdog circuit 41 raises the "EVVI" signal to trigger the third, fixed-rate pacing mode of operation.

When the telemetry circuit 21 asserts the reset, the watchdog circuit 41 is initialized, which includes resetting error flags in a special watchdog status register (part of the watchdog circuit of FIG. 4). This watchdog status register stores eight bits, each acting as an error flag and representing one of the following conditions: watchdog timeout error; multiple acknowledge error; password error; second parity error; first parity error; processor-caused second system reset; and processor-caused first system reset. While reset is asserted, the system remains in the EVVI mode, and the telemetry circuit can write as specific flag byte to predetermined memory location in the internal RAM 38, to put the implantable device in the first, RAM mode. When the reset signal is eventually lowered, the microprocessor 19 executes its reset routine, which causes the microprocessor and its peripheral logic 43 to read the predetermined memory locations to look for the specific flags. If the flags are present, the microprocessor clears the flags and modifies its register 53 value to set the RAM/ROM bit to a logical "1." The microprocessor thereafter operates to check the first vector table to determine where its operating instructions reside.

Importantly, change between modes also causes the patient to be informed of the change using different audible alarms. If the second mode is being used, a first alarm is used to indicate that an error has occurred; if the third mode has been entered, a different alarm informs the patient that an error has occurred; in both cases, the error is urgent and the patient should immediately inform his or her physician. As will be discussed further below, the audible alarm circuit 45 provides these various indications and, further, provides indications of (1) a low battery condition, and (2) the imminent application of anti-tachyarrhythmia therapy. This latter alarm is very important, because anti-tachyarrhythmia therapy can include application to the heart of shocks of several hundred volts, and the patient must be forewarned of its occurrence.

5. Control Over the I/O High Voltage and I/O Chips

The system bus 26 also provides the microprocessor 19 and telemetry circuit 21 with access to both the I/O chip 15 and the high-voltage chip 17.

The I/O chip 15 (FIG. 5) is a self-sufficient chip that remains operating notwithstanding error in the controller chip 13. As mentioned previously, it includes microprocessor-controlled pacing circuitry 29, which takes microprocessor orders to supply stimuli to the heart in each of the first two modes of operation of the implantable device. In addition, monitoring circuitry 27 provides sensed heartbeat information to the microprocessor 19 and to the EVVI state machine 31. Finally, the EVVI state machine takes charge, in the presence of the EVVI signal, to supply fixed-rate pacing when the device is in the third mode.

Figure 5:
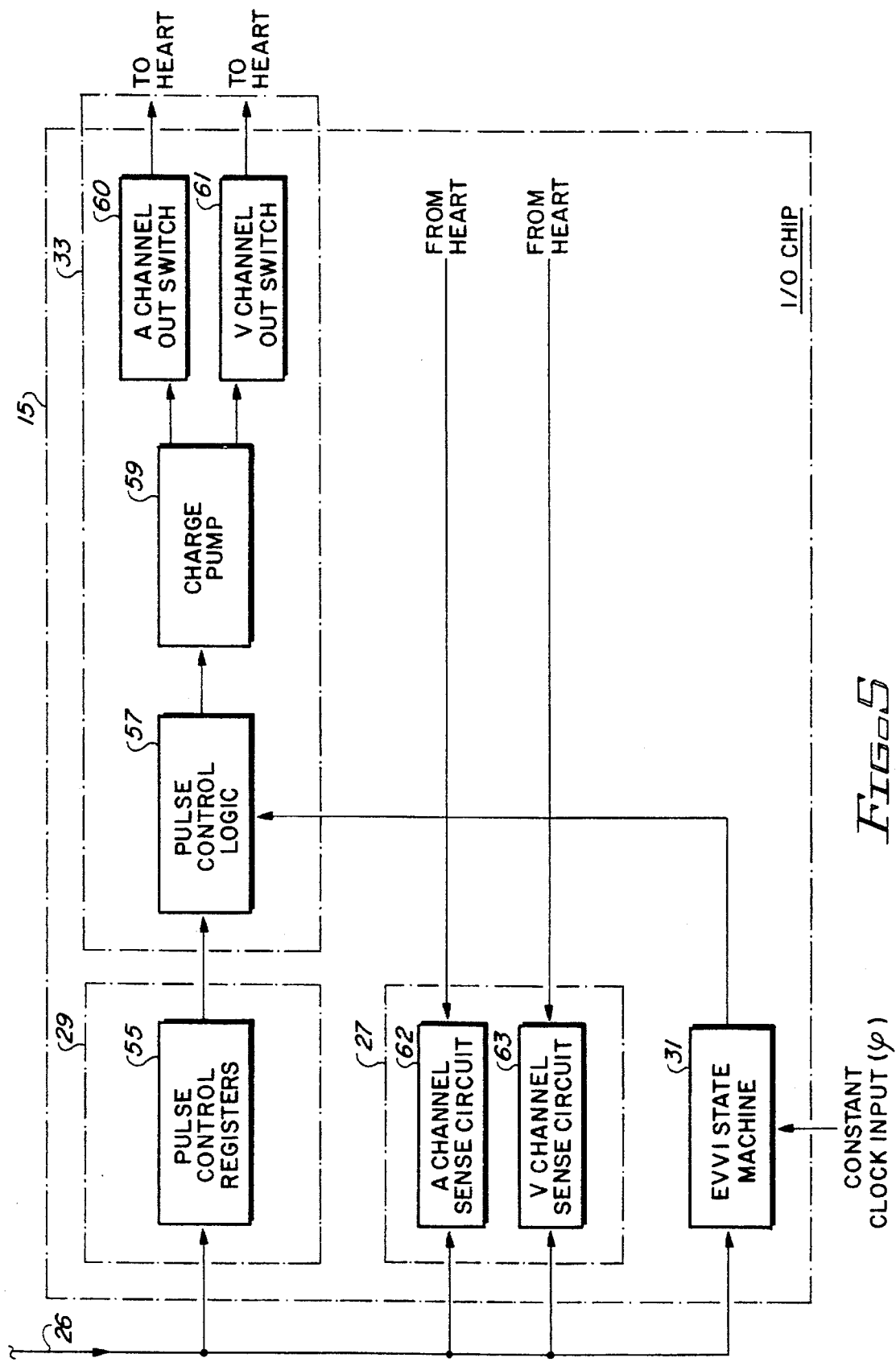
FIG. 5 is a hardware block diagram of the I/O chip 15 of FIG. 1.

As shown in FIG. 5, the microprocessor-controlled pacing circuitry 29 includes a set of pulse control register 55, which receive rate and amplitude instructions from the microprocessor 19. Together with this information and clock signals obtained from the system clock 49 (located on the controller chip 13, FIG. 2), the set of pulse control registers generates amplitude and timing cues that cause the output logic 33 to supply electrical stimuli to the heart, exactly as desired.

The output logic 33 includes pulse control logic 57 for receiving timing and amplitude cues. The pulse control logic controls the charging and release of a charge pump 59, which generates the actual voltages that will be applied to the heart for pacing, as well as for anti-bradycardia therapy and some anti-tachyarrhythmia therapy. The output of the charge pump 59 is gated by output switches 60 and 61, as appropriate, to Output channels for the atrium and the ventricle.

When the implantable device is in the third, EVVI mode, the microprocessor 19 is frozen by the EVVI signal from the watchdog circuit 41 (FIG. 4) and the EVVI state machine 31 is made operational. The EVVI signal will cause the state machine to supply fixed-rate pulses to the pulse control logic 57 (FIG. 5). The EVVI state machine receives a constant clock input φ and, when the EVVI signal from the watchdog circuit is high, the EVVI state machine generates fixed-rate stimuli only if the heart fails to beat on its own within a predetermined interval. Hysteresis rate, EVVI pulse rate, EVVI-mode sense amplitude, and other variables commonly associated with fixed-rate pacing are hardwired inputs provided by the EVVI state machine.

Whichever mode the implantable device is operating in, when it is not supplying stimuli to the heart, the two channels to the heart are monitored by monitoring circuitry 27, including atrial and ventricular sense circuits 62 and 63. These are coupled to the EVVI state machine 31, to assist with demand pacing, as described, and also to the system bus 26, to provide the microprocessor 19 with heartbeat information, which it will use to provide automaticity functions. The microprocessor also can use these sense circuits to apply automatic sensing of thresholds in a well-known manner.

In addition to the I/O chip 15, the microprocessor 19 and telemetry circuit 21 also communicate with the high-voltage chip 17 and its anti-tachyarrhythmia circuit 35 (FIG. 1). If appropriate, in response to sensed heartbeat information provided by the I/O chip 15, the microprocessor can cause the anti-tachyarrhythmia circuit to apply one or more high-voltage shocks to the heart. In the preferred device 11, the second, ROM mode analyzes heartbeats using sudden onset criteria to distinguish pathological tachyarrhythmia from exercise and stress. If the heartbeat quickens in too fast a manner, the sudden onset criteria is satisfied and leads to anti-tachyarrhythmia therapy. Three alternative therapies are preferably provided for use in the second mode, one for each of three tachyarrhythmia heartbeat regions, as will be discussed below. As a result, the microprocessor can gauge whether the tachyarrhythmia is severe and can apply therapy tailored to the particular condition. In the primary mode of operation, the first set of software can be tailored to the particular patient's condition and can provide anti-tachyarrhythmia or anti-bradycardia therapy, as appropriate.

In the paragraphs that follow, the error detection, watchdog, reset, and alarm functions will be further described.

6. The Error Detection Mechanisms

As mentioned above, the implantable device includes an advanced error detecting mechanism. The preferred control unit 11 has three error detection schemes. Two of these schemes, implemented by parity logic 39 and a firmware-based checksum error detecting operation (performed by the microprocessor 19), detect software errors. The third scheme implemented by the watchdog circuit 41, responds to software errors and also detects hardware errors.

a. Handling of Software Errors

The parity logic 39 checks the internal 3K-by-nine bit RAM 38 for errors. The ninth bit of each byte is used as bit storage for odd parity. When a byte of data is written into the RAM, the parity bit is generated and written into the RAM automatically. When a byte of data is read from the RAM, the parity bit is checked against the data being read. A parity error check is performed by the parity logic 39 each time data is retrieved from the internal RAM 38 and, upon occurrence of an error, the parity logic 39 informs the watchdog circuit 41 by sending to it an error signal labeled "PERRINIT" (FIG. 4). Parity logic construction and the use thereof are well known in the electronic arts.

The firmware-based checksum operation regularly checks the sum of the contents of external RAM chip 18. When a checksum error is detected, the microprocessor 19 informs the watchdog circuit 41 via the system bus 26, indicated with the word "DATA" in FIG. 4.

The watchdog circuit 41 handles errors from either of these two mechanisms using logic that generates an error signal. This error signal is sent to the reset logic 50 upon each occurrence of either a parity error or a checksum error. This logic also keeps track of the number of such errors and, upon occurrence of the second error from either the microprocessor 19, the parity logic 39, or a combination of them, it raises a third mode signal, labeled EVVI in FIG. 4, and it maintains this signal in a raised state. The EVVI signal is provided to the EVVI state machine 31 and to the audible alarm circuit 45.

Entering the EVVI state, the watchdog circuit 41 freezes the microprocessor 19 via clock control logic (not shown) (thus preventing it from controlling pacing), activates the EVVI state machine 31 (thus causing it to supply fixed rate pacing in the third mode of operation as described above), and causes the audible alarm circuit 45 to generate a periodic audible alarm, to inform the patient that the third mode has been entered. As mentioned above, the third, EVVI mode can be reset only via the telemetry circuit 21; therefore, if the third mode is entered, the implantable device will stay in that mode until the patient returns to the physician, who can use the telemetry circuit to diagnose the cause of system error. The physician also can load the parameters and/or new software into the internal RAM 38 and external RAM chip 18, if appropriate. As previously mentioned, the telemetry circuit clears the EVVI signal and places the microprocessor 19 once again in the first mode of operation.

b. Hardware Error Detection Using the Watchdog

One portion of software that is always obtained from the ROM 37 and relied upon by the microprocessor 19 is the watchdog acknowledgment routine. The watchdog circuit 41 relies upon real-time counters 51 so that it can time and assert, if appropriate, an active-high signal upon the expiration of each two-second period. Prior to the expiration of the two-second period, it is expected that the microprocessor will execute the watchdog reply routine to send an acknowledgment to the watchdog circuit. If the acknowledgment is properly received, then the watchdog's interrupt counter is cleared and a new two-second watchdog cycle is commenced. However, if the microprocessor has failed to properly acknowledge the watchdog circuit, in the detailed manner that will be described below, then the watchdog circuit raises an error signal (labeled "ERRINIT" in FIG. 4) and the EVVI signal, which it keeps in a raised state, to cause the EVVI state machine 31 to take control of fixed-rate pacing.

With reference to FIG. 4, the particular watchdog scheme used, and in particular, the acknowledgment, is shown to be actually more complicated than in many other digital systems, since the acknowledgment is coded to ensure proper operation of the microprocessor and peripheral logic 43. Each time the microprocessor 19 sends an acknowledgment signal, it retrieves from the watchdog circuit 41 a random password generated by the watchdog circuit for the subsequent acknowledgment (at system initialization, the password is initialized to be "00H"). Further, it calculates one of four address locations from the password, which must be correctly written to in order to reset the watchdog interrupt counter. If the microprocessor fails to write the correct password to the correct location, or if it writes the correct password to more than one location, prior to the next "TIC_INT" pulse, then the watchdog circuit detects a hardware error and places the system in the third mode.

When the microprocessor and peripheral logic 43 have correctly acknowledged the watchdog circuit 41, they retrieve the next randomly generated password and recalculate the associated response location and store these in RAM, continuing with the previously interrupted operation. The watchdog circuit 41 will reset the watchdog interrupt counter if the acknowledgment has been properly performed as described, and it will await the next two-second real time period.

As can be seen, the watchdog circuit 41 perform the important function in the preferred embodiment of directing entry into the hardware-controlled EVVI mode when a hardware error has been detected, or (in cooperation with the microprocessor 19) when a second software error has been detected. It is expected that these two occurrences will constitute exceptional instances, and that the bulk of any errors that might occur will be software errors, handled by entry into the second mode. Importantly, if the microprocessor stops operating for any reason, the watchdog circuit is effective to trigger entry into the third mode, where the EVVI state machine 31 applies fixed-rate pacing.

The error detecting mechanisms of the invention are not limited to use of a parity error check, implemented by the parity logic 39, or the checksum operation, or the watchdog circuit 41. Rather, the error detecting mechanism (within the scope of the invention) can be anything that detects error in logic or a computer circuit. For example, it may also include error correcting codes or cyclical redundancy checksums, or any combination of error detection mechanisms as known in the art. Whatever the error detection mechanism, all that is required is an implantable device that detects error in the first set of operating instructions, or in its execution, and that causes its controller to instead take operating instructions from a different source.

7. The Use of Multiple Alarms

The control unit 11 has different alarms that it preferably uses to alert the patient to the various operating conditions of the implantable device. In accordance with the invention, one alarm alerts the patient that a software error has occurred and that the patient should see his or her physician to have the error investigated and corrected. A different-sounding alarm is used when the device is in the third, EVVI mode, and it indicates that the patient should immediately notify his or her physician and have the situation corrected. Other alarms can be used in response to other conditions of the device, as is discussed below. In the following paragraphs, the alarm circuitry will first be described, followed by the particular alarms utilized in the preferred embodiment.

a. The Alarm Circuitry

The alarms are audibly generated within the control unit, mounted in the patient's chest, by a piezoelectric transducer, which can emit high frequency tones or low frequency vibrations. The actions of the transducer are defined and controlled by a number of factors, including:

(1) Whether the microprocessor 19 is enabled (i.e., the implantable device is operating in one of its first two modes of operation);

(2) Whether the anti-tachyarrhythmia circuit 35 (FIG. 1) is being charged;

(3) The desired duty cycle for the sounding the alarm, which may be loaded by software or hardwired;

(4) Whether the alarm is enabled; and (5) Whether a high frequency tone or a low frequency vibration is generated by the transducer.

These various functions are controlled by loading values into three 8-bit alarm control registers 65, 67 and 69 (8060–8062 hex, illustrated in terms of the bit-function in FIGS. 8–10), and alarm logic drives the alarm, as described below, in response to the values stored in these registers. The registers preferably are written to by the microprocessor 19, to allow software to define the parameters of the alarm, and they also have corresponding hardwired values for use in the third, EVVI mode.

Figure 8:
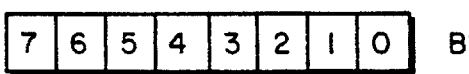
FIG. 8 indicates functions associated with the various bits of a first alarm control register (8060 hex).
Figure 9:
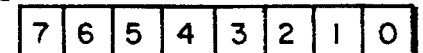
FIG. 9 indicates functions associated with the various bits of a second alarm control register (8061 hex).

Referring first to FIGS. 8 and 9, the first two of the three alarm control registers 65 and 67 are used to set the nature of the tone to be emitted by the piezoelectric transducer.

First, the duty cycle for the alarm is set as follows. Referring first to FIG. 8 (alarm control register 1), the five LSBs control the length of time for which the piezoelectric transducer receives a high signal; by contrast, in FIG. 9 (alarm control register 2), the five LSBs indicate the amount of time that the piezoelectric transducer receives a low signal. Between these two groups of five bits, a duty cycle is defined for the alarm to drive either the high or low tone.

Second, the high frequency tone that can be emitted by the transducer is exactly 64 times higher in frequency than the low frequency tone, and it is selected by writing a logical "1" to the first MSB of alarm control register 2 (FIG. 9).

As to the rest of alarm control register 1 (FIG. 8), the most significant bit (MSB) switches the alarm on when loaded with a logical "1" value and causes the transducer to vibrate. The second MSB is normally loaded with a logical "0" to provide selective microprocessor-control for the alarm, but it is overridden by the anti-tachyarrhythmia circuit 35 to provide a high-voltage charge alarm, indicating that the patient should stop all hazardous activities, such as driving a car, in preparation for a shock. The tones for this latter alarm are defined by hardware, and they are generated after the microprocessor 19 has determined that anti-tachyarrhythmia shocks are necessary and has directed the high-voltage chip 17 to begin storing energy for a large shock to be delivered to the heart. In accordance with common practice, the patient can be provided with a magnet that can be used to forestall the large shock until the patient is prepared for it.

Figure 10:
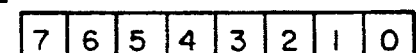
FIG. 10 indicates functions associated with the various bits of a third alarm control register (8062 hex).

The third alarm control register, as indicated in FIG. 10, includes two MSBs, which can be read and written to by the alarm control circuit 45, and six status bits that can be read by the microprocessor 19 or the telemetry chip 21. The first MSB is written to by the alarm control circuit 45 to raise it to a logical "1" when the "EVVI" signal has been raised, indicating the implementation of hardware-controlled pacing and deactivation of the microprocessor. The second MSB is used to provide an alarm "blip" of short duration, but this latter alarm is generally used only for testing purposes.

b. The Particular Alarms Used by the Preferred Software, in each of the First and Second Modes The aforementioned registers and circuitry permit selection of five different alarm modes by the alarm control logic.

First, whenever the implantable device enters the third mode, indicating hardware-controlled pacing and no anti-tachyarrhythmia or bradycardia functions, an alarm is sounded that consists of a 250 millisecond, 819-hertz beep and a two-second, 12.7-hertz vibration, both occurring together every eight minutes and 32 seconds. The sounding of this alarm indicates that the patient should return to the physician's office, because hardware-controlled pacing has been implemented as a backup caused by failure of the microprocessor 19, likely a hardware failure.

In a second alarm condition, the microprocessor 19 can sound the aforementioned "blip," which provides a high-frequency tone lasting for 62.5 milliseconds. This "blip" can be used for testing or to indicate system status, as might be desired in a particular implementation. It has not been implemented to represent a particular condition in this preferred embodiment, however.

In a third alarm condition, a high-voltage charge alarm, different from the EVVI alarm, is sounded. This alarm consists of a series of 62.5-millisecond high pitch tone bursts superimposed on a low pitch tone vibration. As mentioned above, the sounding of this alarm indicates to the patient that the high voltage chip's anti-tachyarrhythmia circuit 35 has been activated and is preparing to deliver a large shock to the heart.

The fourth alarm condition is entered when the microprocessor 19 exits the first, RAM mode and enters the second, ROM mode, indicating a detected software error that should be reported to the physician, who may wish to see the patient. This alarm also is sounded if a low battery condition has been detected by the microprocessor.

Finally, the microprocessor 19 can, in proper functioning of its programming, indicate a microprocessor-controlled EVVI alarm, such as to indicate a different error, or otherwise to inform the patient that he or she should return to the physician's office; i.e., for a periodic checkup. This mode also has not been implemented in (i.e., called by the software of) the preferred embodiment.

8. Arrhythmia Detection and Therapy

Arrhythmia detection and therapy is one of the automaticity features of the present invention, and is provided for not only in the normal, RAM mode, but also in the backup, ROM mode. In each of these modes, arrhythmia is detected by analyzing heartbeat rate and classifying it into a zone identified by Table I, below, determining and applying appropriate therapy, and determining when the criteria for termination have been satisfied. Further, therapy can consist of pacing stimuli, applied by the I/O chip 15, or high-voltage shocks, applied by the high-voltage chip 17. These options will be explained below, accompanied by an explanation of some of the programmable features of the anti-tachyarrhythmia scheme provided in the backup mode.

Importantly, although the microprocessor 19 only executes the code stored in the ROM 37, its features can be programmably defined using the telemetry circuit 21. In particular, when operating in the second, backup mode, the microprocessor still retains a minimal work space in the internal RAM 38, for stack and data storage, and telemetry can be used to configure operating parameters using the internal RAM 38. Indeed, telemetry can be used to program a number of features of the arrhythmia rate zones, as will be discussed below, after the device enters the ROM mode. Parameters can be changed after the device enters the ROM mode by using telemetry to store parameters in the internal RAM 38.

a. Zone Scheme

The second, ROM mode provides anti-tachyarrhythmia abilities for each of four arrhythmia rate zones. As mentioned above, this scheme (indicated in Table I) preferably will be made factory-standard for the implantable device. Software for the first, RAM mode can be made either to duplicate this particular scheme or to implement a different scheme, such as providing specialized bradycardia therapy, etc. By communicating through the telemetry chip 21, a physician can selectively disable tachyarrhythmia zones ("VT1" and "VT2") by writing a predetermined command to a specific location in the internal RAM 38. In this event, there is no discontinuity in the scheme shown in Table I, and the criteria for the disabled zone are subsumed by the immediately higher-order enabled zone.

TABLE I

| Rate Zone | Lower Limit | Upper Limit |
| --- | --- | --- |
| VF | 240 BPM | NA |
| VT2 | 200 BPM | 240 BPM |
| VT1 | 150 BPM | 200 BPM |
| NORMAL SINUS | 50 BPM | 150 BPM |
| BRADYCARDIA | NA | 50 BPM |

Figure 11:
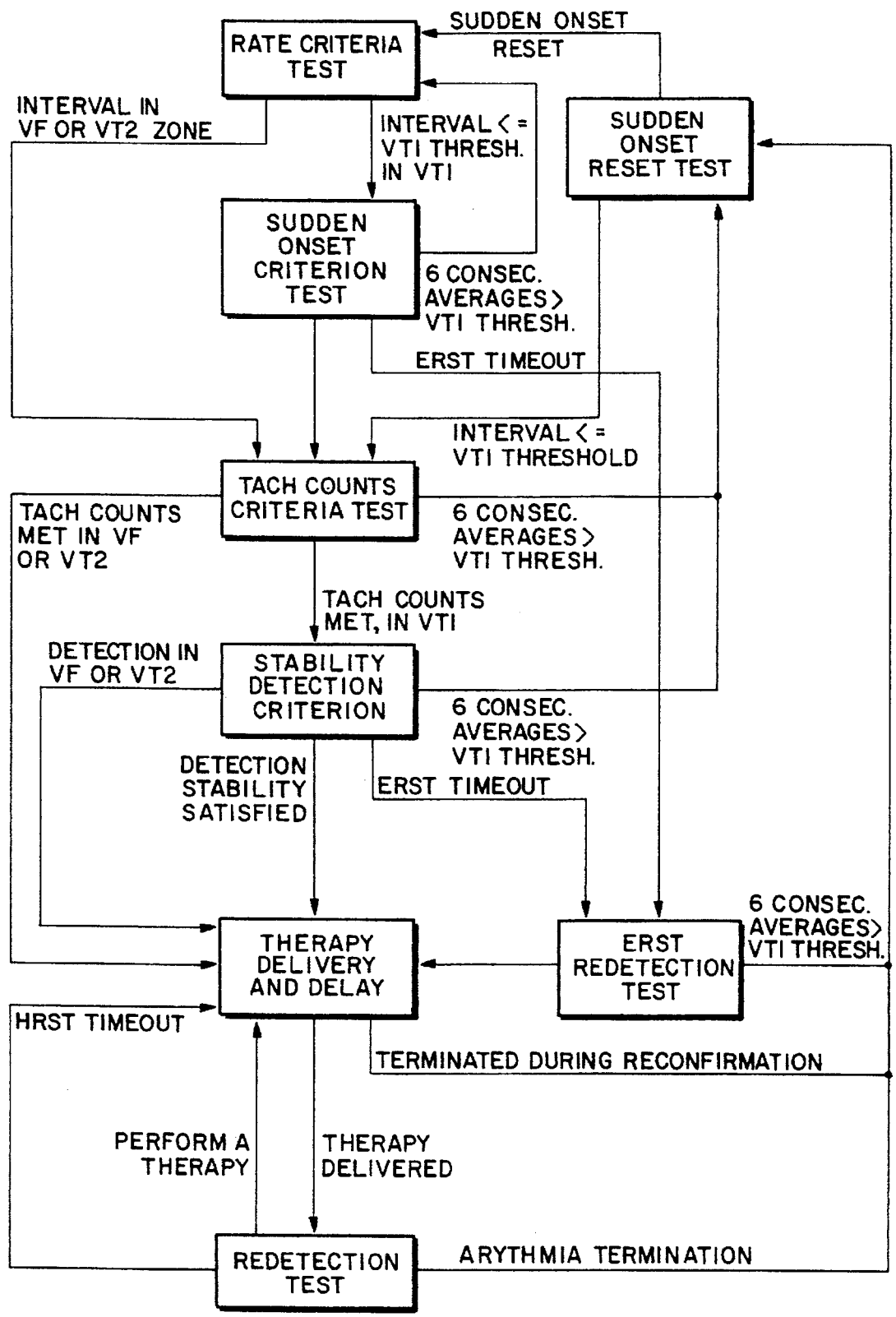
FIG. 11 is a software block diagram of anti-tachyarrhythmia functions used in the preferred implantable device.

Importantly, tachyarrhythmia and bradycardia therapy and diagnosis are well known in the art, and a detailed understanding of their operation is not considered essential to an understanding of the present invention. However, for purposes of illustration, tachyarrhythmia diagnosis and therapy will be briefly explained with reference to FIG. 11.

b. Tachyarrhythmia Detection

The backup, ROM mode distinguishes exercise and physiological tachyarrhythmia from tachyarrhythmia by analyzing the heartbeat rate for sudden onset. The microprocessor 19 computes an average time interval between the four most recent. If the time interval to the next heartbeat occurs quickly enough that it represents a tachyarrhythmia rate (see Table I), and if it is also less than a predetermined percentage of the four-interval average, then sudden onset is detected. Using this procedure, a fast heartbeat caused by stress or exercise may be differentiated, because it quickens in a slower manner than a dangerous heart condition.

Importantly, the sudden onset criteria is applied only to the lowest enabled tachyarrhythmia zone, generally that labeled "VT1" in Table I, above. A single interval satisfying the criteria for a higher-order zone will trigger therapy appropriate for that zone. After a tachyarrhythmia has been detected, the microprocessor 19 will analyze to determine if the tachyarrhythmia has ended. The microprocessor must determine that eight consecutive heartbeat intervals falling below any tachyarrhythmia zone have elapsed. In addition, the microprocessor must determine that six consecutive averages of the four most recent heartbeat intervals produce times below the lowest tachyarrhythmia threshold.

In addition to the use of sudden onset, the implantable device provides a number of programmable features that enable a physician to vary the type of tachyarrhythmia detection and therapy provided in the second, backup mode. For example, stability detection criteria can be implemented for tachyarrhythmia rate zones as either "detection," "stability" or "off." If "detection" is the programmed value, then an arrhythmia is not detected until the stability criteria, mentioned below, has been satisfied for that particular zone. If "therapy" is the programmed value associated with the stability criteria for the particular zone, then either anti-tachyarrhythmia therapy or alternative high voltage shocks may be applied, depending upon whether the stability criteria are satisfied. For example, if in conjunction with the use of sudden onset detection, a tachyarrhythmia is detected as being stable within the "VT2" zone, then anti-tachyarrhythmia therapy might be advisable for the particular patient's condition.

Alternatively, if for the particular patient high variance in heart rate is indicative of a malignant condition, then failure to meet the stability criteria for the particular tachyarrhythmia zone might require the application of high voltage shocks, as opposed to specialized anti-tachyarrhythmia therapy. Finally, stability criteria may be programmed as "off" for the particular zones.

Stability as used in connection with the backup software of the implantable device, is defined as the lack of variance in heartbeat rate. If the variance for six consecutive four-heartbeat interval averages is less than or equal to a predetermined time period, then tachyarrhythmia rate zones are enabled, and each average is grouped according to zone until a number of six averages falls within one zone. Thus, once the low variance triggers stability analysis, the stability criteria is satisfied when six instances are identified in a particular zone. The bins used to count these averages are then cleared for subsequent stability detection.

All of the above-mentioned programmable features, along with the other programmable features discussed herein, can be set using the telemetry circuit 21, which writes a predetermined code to a specific RAM location while telemetry has control of the system. As mentioned earlier, as telemetry releases control of the system, a reset of the microprocessor 19 is triggered and the microprocessor checks the internal RAM 38 for the presence of these codes, clearing them as it does so. The start-up software of the microprocessor causes it to do this and appropriately configure its registers (not shown) for operation of the device 11 when it is in the second, backup mode. Accordingly, at the time of implantation, the telemetry circuit can be used not only to put the implantable device into a first operating mode, but also to select particular anti-tachyarrhythmia detection and therapy as might be appropriate for the particular patient.

c. Tachyarrhythmia Therapy

Therapy is preferably separately handled by software for each of the "VT1" and "VT2" rate zones specified in Table I, whereas zone "VF" corresponds to ventricular fibrillation, and defibrillation is always applied using the high-voltage chip 17. Within these zones, three different stages of therapies can be applied, and any of these therapies can be enabled or disabled, as can the particular rate zone. Importantly, if a tachyarrhythmia zone is disabled, sudden onset and stability criterion are applied to the next-highest rate zone, e.g., "VT2."

When tachyarrhythmia is detected in a particular zone, the implantable device begins to apply first stage anti-tachyarrhythmia therapy, then second stage, then third stage, if these stages are enabled, until an end to tachyarrhythmia has been determined, or a higher rate zone has been detected. For example, when tachyarrhythmia is detected within the "VT1" zone, a number of 0.25–11 volt pulses can be applied by the I/O chip 15 to the "R-wave" of the heartbeat at a programmable amplitude and duration. The number of stimuli (1–15) can be programmed, as well as the interval between applying a second stage of therapy if tachyarrhythmia is not ended. The second stage of therapy has the same programmable parameters as does the first, and may be programmed using the telemetry circuit 21, in response to the particular patient's condition.

Each of the "VT1" and "VT2" zones has an associated real-time counter 51 (FIG. 3), and after the third stage of therapy has been given, no further therapy is given. Expiration of the associated timer (without a detected end to tachyarrhythmia or reclassification as part of a higher zone) automatically causes entry into the higher zone (i.e., either "VT2" or "VF").

Alternatively, therapy can include from 1 to 7 high-voltage shocks, applied by the high-voltage chip 17. These shocks are programmable in voltage (56–756 V), shock numbers (1, 2, 3 and 4–7), and duration. In addition, shock morphology can also be programmable as monophasic or bi-phasic, as is known in the art. Following the application of shock therapy, the rate bins and counters are blanked and no therapy is provided for a programmable amount of time, which is at least one second. Thereafter, bradycardia therapy is provided, e.g., demand pacing.

d. Tachyarrhythmia Termination

During the time that a tachyarrhythmia has been detected, a count is kept of the number of consecutive averages that occur below the lowest programmed tachyarrhythmia rate zone. A single average falling within an enabled tachycardia zone of Table I breaks this count, and causes it to begin again. If six consecutive averages fall below the lowest enabled tachycardia zone (i.e., the count reaches 6), then classification within the particular tachycardia zone is considered to be terminated. If, in addition, eight consecutive heartbeat periods falling below any tachyarrhythmia zone have elapsed, then tachyarrhythmia is considered ended.

9. Alternative Embodiments

The present invention is not limited to the use of instruction sets that are stored in the ROM 37 and the internal RAM 38. All that is required is that two alternative sets of instructions be available for additional reliability in case of error, and any type or number of memory elements can be used to make those instructions available.

One alternative embodiment presently contemplated is to use a RAM to store the first set of operating instructions for the microprocessor 19, and a second memory that stores the second set of software in a compressed format. Upon detecting an error, the microprocessor would operate to reboot, decompress the compressed, second program set, and write the newly de-compressed second program set into RAM, to thereby overwrite the first program set. The program memory for storing the second, compressed set of program instructions could simply be another ROM, and such a system would be, in terms of its schematic representation, exactly like that shown in FIG. 1. The notable exception to this, however, is that code for decompressing the second set of software and loading it into RAM would preferably be itself stored in an additional ROM.

In addition, the present invention is not limited to the use of providing a particular backup therapy, e.g., tachyarrhythmia pacing or shocks, but can include any automaticity or desired functions that would normally be lost when the microprocessor 19 is shut down in response to a detected error. As another contemplated alternative embodiment, the second set of software stored in the internal ROM 37 can provide primarily for sophisticated anti-bradycardia therapy, or other particular therapy, as appropriate.

Having thus described several exemplary embodiments of the invention, it will be apparent that various alterations, modifications, and improvements will readily occur to those skilled in the art. Such alterations, modifications, and improvements, though not expressly described above, are nonetheless intended and implied to be within the spirit and scope of the invention. As one example, the hardware features of the present invention can be implemented as software features, and vice-versa, without departing from the scope of the invention. Accordingly, the foregoing discussion is intended to be illustrative only; the invention is limited and defined only by the following claims.

APPENDICES

Attached hereto as Appendix "A" is a memory map for the preferred device 11.

Attached hereto as Appendix "B" is a Interrupt Vector ROM summary for the preferred device 11.

APPENDIX A

GENERAL MEMORY MAP

| | | ADDRESS | DESCRIPTION | SIZE | |
|---|---|---|---|---|---|
| 128K External RAM | | 0000h<br>00FFh | Page 0 | 256 Bytes | |
| | | 0100h<br>01FFh | Page 1 Stack | 256 Bytes | |
| | | 0200h<br>02FFh | Telemetry Buffer/General RAM | 256 Bytes | |
| | | 0300h<br>3FFFh | External RAM common area for code, parameters. | 15616 Bytes | |
| | | 4000h<br>7FFFh | Data Banks 1 through 7 are all mapped into this address range. Each bank contains 16K bytes. | 16K Bytes | |
| | | 8000h<br>80FFh | Internal Hardware Registers & Vector ROM | 256 Bytes | |
| | | 8100h<br>81FFh | External I/O 1 (HVC) | 256 Bytes | |
| | | 8200h<br>82FFh | External I/O 2 (EIO) | 256 Bytes | |
| | | 8300h<br>83FFh | External I/O 3 (RSVD) | 256 Bytes | |
| | | 8400h<br>84FFh | External I/O 4 (RSVD) | 256 Bytes | |
| | | 8500h<br>9FFFh | Reserved Hardware Address Space | 6912 Bytes | |
| | | A000h<br>BFFFh | 8K External ROM | 8192 Bytes | |
| 3K Internal RAM | Page C0<br>To<br>Page CB | C000h<br>C01Fh | Product ID's. Model #, and Serial # | 32 Bytes | (Read only for Processor,<br>Read/Write for Telemetry) |
| | | C020h<br>CBFFh | Internal RAM | 3040 Bytes | |
| | | CC00h<br>FFFFh | Not used in the current Rev. | 14336 Bytes | |

APPENDIX B

Interrupt Vector ROM

| Address | Name | Type | Reset Condition | Reset Value | Description |
|---|---|---|---|---|---|
| 80E0h<br>I<br>80FFh | Vector ROM | R | N/A | N/A | The vector rom contains two sets, of 32-byte interrupt vectors. Both sets of vectors are mapped to the same address range. The RAM_ROM* bit in the control register 1 does the selection. |

What is claimed is:

1. An implantable cardiac stimulation device, comprising:

sensing means for sensing a physiological parameter of a patient;

pulse generating means for providing stimulation pulses to the patient's heart;

control means, coupled to the pulse generating means and responsive to the sensing means, for controlling at least one of amplitude and timing of the stimulation pulses;

means, coupled to the control means, for storing two alternative sets of instructions that, when executed, determine operation of the control means, the two alternative sets of instructions each provide a normal mode of operation; and error detection means for detecting errors in the operation of the implantable cardiac stimulation device;

wherein the control means includes:
means for operating in a first mode of operation using a first set of instructions, and means for switching to a second mode of operation using the alternative set of instructions in the event that an error is detected in the first mode of operation.

2. The device according to claim 1, wherein:

the sensing means provides an indication of heart rate; and the two alternative sets of instructions each include a routine for detecting tachyarrhythmia and for applying anti-tachyarrhythmia therapy.

3. The device according to claim 1, wherein:

the sensing means provides an indication of metabolic demand; and the two alternative sets of instructions each include a routine for applying rate-responsive pacing therapy.

4. The device according to claim 1, wherein:

the two alternative sets of instructions each include a routine for applying automatic modes of pacing therapy.

5. The device according to claim 1, wherein:

the sensing means provides an indication of heart rate; and the two alternative sets of instructions each include a routine for detecting bradycardia and for applying anti-bradycardia therapy.

6. The device according to claim 1, further comprising:

timing means, triggered by the error detection means detecting an error in the second mode of operation, for by-passing the control means and for triggering stimulation pulses at a fixed-rate in a third mode of operation.

7. An implantable cardiac stimulation device, comprising:

sensing means for sensing a physiological parameter of a patient;

control means, in response to the sensing means, for providing an output signal indicating one of timing and amplitude of a stimulation pulse in accordance with a set of stored instructions;

pulse generating means for providing stimulation pulses to the patient's heart in response to the output signal;

first memory means for storing a first set of instructions that, when executed, controls operation of the control means based on the sensed physiological parameter;

second memory means for storing a second set of stored instructions that, when executed, controls operation of the control means based on the sensed physiological parameter; and error detection means, operatively coupled to at least one of the control means and the first memory, for detecting the occurrence of an error in operation of the device, to thereby detect possible corruption of the first set of stored instructions, the error detection means providing an error indication in response thereto;

wherein the control means includes:

means for operating in a first mode of operation in response to the first set of stored instructions when there has been no error indication, and means for operating in a second mode in response to the error indication in which its operation is governed by the second set of stored instructions;

whereby the control means continues to control the operation of the device based on-the sensed physiological parameter of the patient, notwithstanding the error indication.

8. The device according to claim 7, further comprising:

alarm means, triggered by a change from the first mode to the second mode, for notifying the patient of such change.

9. The device according to claim 8, wherein the device further comprises:

timing means, triggered by the detection of an error in the second mode of operation, for by-passing the control means and for triggering stimulation pulses at a fixed-rate in a third mode of operation; and wherein the alarm means includes means for notifying the patient of a change from the second mode to the third mode of operation.

10. The device according to claim 7, wherein:

the error detection means includes means for detecting occurrence of a second error in operation of the device, to thereby detect a second possible corruption of stored instructions, and for supplying a second error indication in response thereto; and the device further includes timing means, independent of the control means, for triggering stimulation pulses to be delivered in a third mode of operation in response to the second error indication, the third mode of operation enabling a fixed-rate of stimulation pulses to be generated by the pulse generating means.

11. The device according to claim 10, wherein:

the sensing means includes a heart rate sensing means; and the timing means, in response to the heart rate sensing means, includes means for generating the fixed-rate stimulation pulses on a demand basis.

12. The device according to claim 10, wherein the device further comprises:

watchdog means, coupled to the control means, for periodically receiving correct acknowledgment from the control means and, if no correct acknowledgment is received, for disabling the control means and for enabling the timing means to trigger stimulation pulses in the third mode.

13. The device according to claim 12, wherein:

the watchdog means includes means for triggering the device to change to the third mode whenever more that one acknowledgment is received for a predetermined period associated with each correct acknowledgment.

14. The device according to claim 7, wherein the device comprises:

storing means for storing data that determines the mode of operation of the control means;

telemetry means for selectively receiving communication from the exterior of a body in, which the device is implanted, the telemetry means adapted to change the data stored in the storing-means in response to selective communication, the telemetry means including means for triggering the device to change dependence of the control means upon one of the first and second sets of stored instructions to the other.

15. The device according to claim 7, wherein:

the sensing means is a heart rate sensing means that provides an input signal representing heart rate;

the control means, upon executing the first set of instructions, includes means for monitoring the input signal to detect at least one of a tachyarrhythmia and a bradycardia condition;

the control means, upon executing the second set of instructions, includes means for monitoring the input signal to detect at least one of a tachyarrhythmia and a bradycardia condition; and the device further comprises anti-arrhythmia means for applying anti-arrhythmia therapy to the heart in response to detection of the condition.

16. The device according to claim 15, wherein:

the device further comprises means for detecting at least two different gradations of tachyarrhythmia; and the control means, upon executing the first set of instructions in the first mode, includes means for applying a different anti-tachyarrhythmia therapy to the heart for each of the at least two different gradations.

17. The device according to claim 16, wherein:

the control means, upon executing the second set of instructions in the second mode, includes means for applying a different anti-tachyarrhythmia therapy to the heart for each of the two different gradations.

18. The device according to claim 17, wherein:

at least one gradation of tachyarrhythmia in each of the first and second modes corresponds to a fibrillation condition; and the first and second sets of instructions each include instructions that, when executed, trigger the control means to deliver defibrillation therapy to the heart.

19. The device according to claim 7, wherein the first memory means includes a random access memory and the second memory means includes a read-only memory.

20. The device according to claim 19, wherein:
the control means includes means, in response to a third set of instructions stored in the read only memory, for loading the second set of instructions from the second memory means into the first memory means, to thereby effect a change from the first mode to the second mode.

21. The device according to claim 20, wherein:
the second set of instructions is stored in the second memory means in compressed form; and
the control means, upon a change to the second mode, includes means for decompressing the second set of instructions prior to loading it into the first memory means.

22. The device according to claim 7, wherein the device further comprises:
a different memory address pointer for each of the first and second modes, wherein the memory address pointer for the first mode refers the control means to the first memory means, and wherein the memory address pointer for the second mode refers the control means to the second memory means.

23. The device according to claim 7, wherein the error detection means includes at least one of:
parity checking means for checking parity of each operating instruction of at least the first set of instructions; and
checksum means for performing checksum analysis on operating instructions stored in the first memory at least when the control means is operating in the first mode.

24. The device according to claim 7, wherein:
the device further comprises a fixed-rate timing means, implemented in hardware, for determining a fixed-rate mode for delivering stimulation pulses independent of the control means;
the pulse generating means includes means for generating stimulation pulses based on one of the first set of instructions, the second set of instructions, or the fixed-rate timing means; and
the error detection means includes parity checking means for determining the existence of a first parity error by checking parity of at least some data utilized by the control means, wherein the operation of the control means in response thereto is switched from the first mode to the second mode, and
the error detection means further includes means for subsequently detecting the existence of a second parity error by checking parity of at least some data utilized by the control means, whereupon the pulse generating means is triggered to enter the hardware-controlled fixed-rate mode.

25. The device according to claim 24, wherein the device includes means for operating as a demand pacemaker when it is in the hardware-controlled fixed-rate mode.

26. An implantable cardiac stimulation device, comprising:
error detection means for detecting errors;
telemetry means for producing a digital signal responsive to communication received from outside the body;
control means for determining at least one of timing and magnitude of stimulation pulses in response to each of two alternative sets of stored program instructions, a first set being associated with a first mode and a second set being associated with a second mode;
watchdog means, in communication with the control means, for requiring the control means to acknowledge proper operation;
pulse generating means for generating stimulation pulses supplied to the heart in response to one of the control means and the watchdog means;
timing means, selectively activated by the watchdog means, for triggering the pulse generating means to generate stimulation pulses at a fixed rate independent of the control means; and
processing means for controlling the pulse generating means to deliver stimulation pulses with a hierarchy of pacing modes, the processing means including:
means for controlling the pulse generating means to operate in a first mode corresponding to a first level of the hierarchy which includes telemetry control, wherein the digital signal provides the telemetry means with the ability to selectively place the control means in at least the first mode based upon the first set of stored program instructions;
means for controlling the pulse generating means to operate in a second pacing mode corresponding to a second level of the hierarchy which includes watchdog control, wherein the watchdog means includes means for triggering the pulse generating means, when correct acknowledgment is not received, to generate the stimulus in accordance with the fixed-rate timing means and not in response to the control means; and
means for controlling the pulse generating means to operate in a third pacing mode corresponding to a third level of the hierarchy which includes error detection control, wherein the error detection means includes means for triggering the control means to switch from the first mode to the second mode, and thereby rely upon the second, alternative set of stored program instructions in response to error detected in the first mode.

27. A method for controlling an implantable cardiac stimulation device to provide an electrical stimulus to the heart, the method using a control means, an error detection means and at least two areas of memory that each have a set of stored instructions that direct actions by the control means, the method comprising the steps of:
executing a first set of the stored instructions to direct the actions of the control means in providing the stimulus to the heart, the first set of stored instructions providing at least one automatic function;
detecting errors in operation of the implantable cardiac stimulation device using the error detection means; and
executing a second set of the stored instructions in response to the detection of an error, so that the actions of the control means in providing the stimulus are determined by the second set of stored instructions which also provides at least one automatic function.

28. The method according to claim 27, wherein the method further uses two alternate memory address pointers, one pointing to the location in memory of the first set of instructions and the other memory address pointer pointing to the location in memory of second set of instructions, further comprising the steps of:
triggering the control means, in a first operating mode of the device, to retrieve operating instructions using the first memory address pointer; and triggering the control means, in response to the detection of error, to enter a second mode of the device, where the control means retrieves the operating instructions using the second memory address pointer.

29. The method according to claim 27, wherein the method further uses a fixed-rate timing means, further comprising the steps of:

detecting whether a second error has occurred during the executing of the second set of the stored instructions;

disabling the control means, in response to the occurrence of a second error, from controlling the timing of the stimulus to the heart; and enabling the fixed-rate timing means to provide the timing for the delivery of the stimulus in a demand mode.

30. The method according to claim 29, wherein the method further uses an alarm device, the method further comprising the steps of:

alerting the patient, using the alarm device, of a switch to the second mode; and alerting the patient, using the alarm device, of a switch to the third mode.

31. The method according to claim 29, wherein the method further uses a watchdog circuit that-monitors the control means, the method further comprising the steps of:

periodically checking the watchdog timer for an acknowledgment that the device is functioning properly; and triggering a third mode to be entered if the periodic acknowledgment is not received from the watchdog.

32. The method according to claim 27, wherein the method further uses an alarm device, the method further comprising the steps of:

alerting a patient of the occurrence of an error.

* * * * *